United States Patent [19]

Byers et al.

[11] Patent Number: 4,991,582

[45] Date of Patent: Feb. 12, 1991

[54] HERMETICALLY SEALED CERAMIC AND METAL PACKAGE FOR ELECTRONIC DEVICES IMPLANTABLE IN LIVING BODIES

[75] Inventors: Charles L. Byers, Canyon Country; James W. Beazell, Rancho Palos Verdes; Joseph H. Schulman, Granada Hills; Ali Rostami, Santa Monica, all of Calif.

[73] Assignee: Alfred E. Mann Foundation for Scientific Research, Sylmar, Calif.

[21] Appl. No.: 411,403

[22] Filed: Sep. 22, 1989

[51] Int. Cl.⁵ ............................................. A61N 1/00
[52] U.S. Cl. ............................. 128/419 P; 128/419 R
[58] Field of Search ............... 128/419 R, 419 P, 903, 128/631, 418 F; 29/825, 830

[56] References Cited

U.S. PATENT DOCUMENTS

| 4,248,237 | 2/1981 | Kenny | 128/419 P |
| 4,262,673 | 4/1981 | Kinney et al. | 128/419 P |
| 4,399,819 | 8/1983 | Cowdery | 128/419 P |
| 4,919,135 | 4/1990 | Phillips, Jr. et al. | 128/419 P |

Primary Examiner—Lee S. Cohen
Assistant Examiner—S. Getzow
Attorney, Agent, or Firm—Robert R. Meads

[57] ABSTRACT

A hermetically sealed combination ceramic and metal package for electronic components of an electronic device implantable in a living body, at least some of the components being adversely affected by high temperatures. The package comprises a ceramic sleeve and a metal band having substantially the same coefficients of linear thermal expansion. An annular end face of the sleeve butts against and hermetically seals to an annular end of the metal band. A header plate carrying a substrate upon which the components are mounted and a plurality of electrical connectors closes the open end of the sleeve and is hermetically sealed to the metal band.

24 Claims, 4 Drawing Sheets

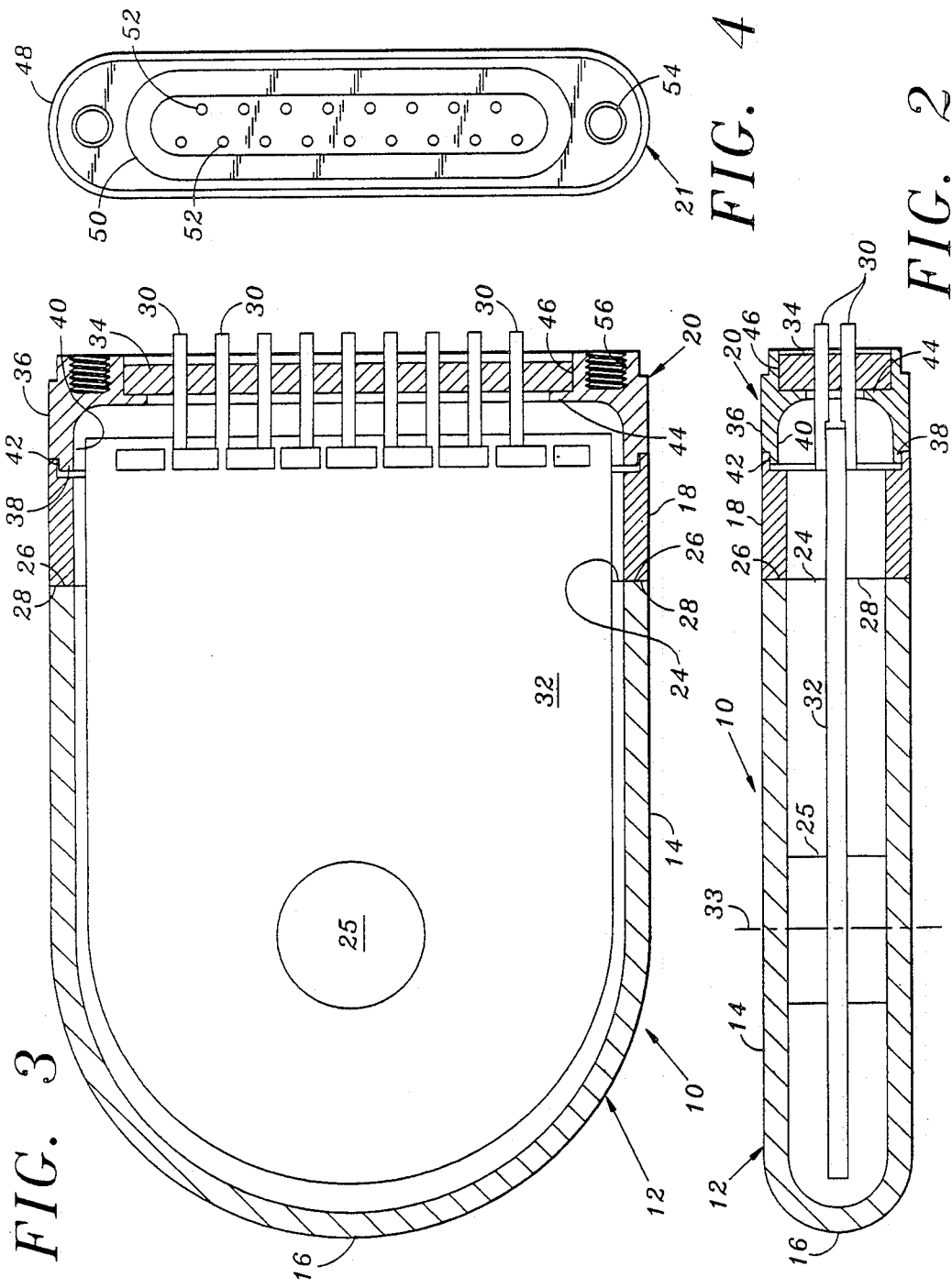

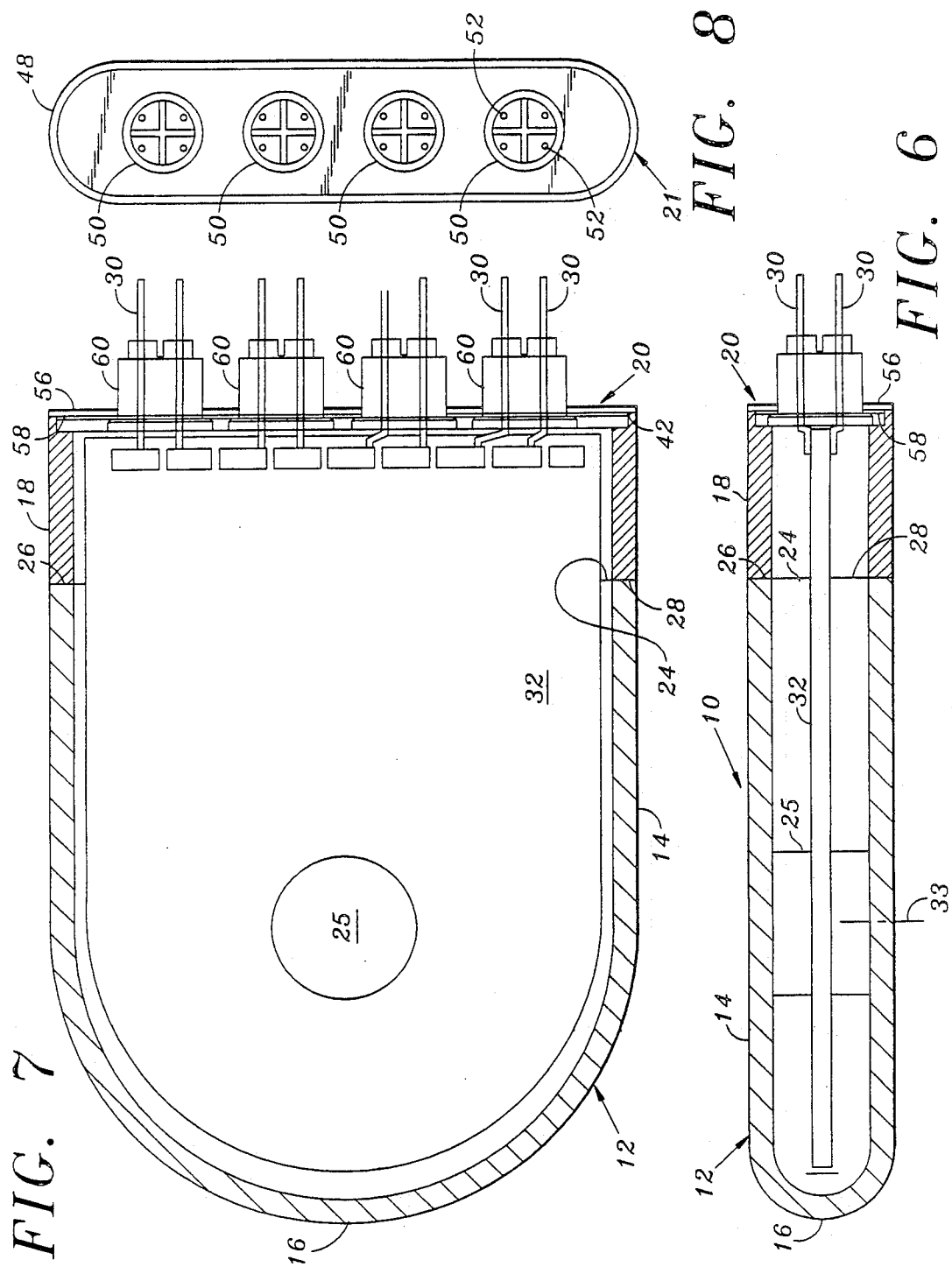

HERMETICALLY SEALED CERAMIC AND METAL PACKAGE FOR ELECTRONIC DEVICES IMPLANTABLE IN LIVING BODIES

BACKGROUND

The present invention relates to improvements in electronic devices implantable in living bodies and more particularly to an improved hermetically sealed package for housing such electronic devices.

Stimulators which are to be implanted in living bodies and powered from external information sources must be housed in packages of biocompatible material. Such packages must protect the electronic circuitry within the implanted stimulator from body fluids and ions so that the circuitry can survive for extended periods without any significant changes in performance.

Early efforts at packaging implantable electronic devices, beginning with miniature radio telemetry units in 1957 and cardiac pacemakers in 1958, employed polymer packages. For the next 15 years, the field of implant packaging was dominated by polymers, principally epoxies, elastomers, and Teflon. Unfortunately, implant failures were common with such packages. Finally, it became clear that packages formed even in part of polymers when implanted in living bodies did not provide a permanent barrier to water which passed through the polymer compounds as water vapor and condensed in cavities or on the surfaces of electronic components housed in such packages.

Besides water leakage, polymer packaging presents other disadvantages. Hard polymer materials, such as epoxies, tend to change volume during curing, often shrinking and exerting damaging stresses on components of a polymer package. Also, water, lipids and other components of body fluids may be absorbed by such polymers causing delayed volume changes and package damage. In addition, sometimes polymers evolve gases or acids during curing while some non-adherent coatings, like Teflon, form channels that can quickly wick fluids by capillary action to the most vulnerable circuit components of the implanted stimulator. Such problems exist even when a polymer is only part of a packaging system that includes a hermetic capsule for electronic components. Also, it has been found that polymer coatings sometimes limited or prevented effective hermeticity leak testing of a metal, glass or ceramic portion of a packaging system because of out-gassing from the polymer. In view of such shortcomings, polymer encapsulation is no longer considered an acceptable packaging technique for chronic implants. For example, all pacemakers are now hermetically sealed in metal packages.

In that regard, in the early 70's, the first commercially successful hermetically sealed in metal pacemaker was introduced. Today, the most commonly used metals for implantable packages are titanium, stainless steel and cobalt-chromium alloys. These metals are biocompatible and corrosion resistant. Normally, the package consists of two parts welded together to insure hermeticity. The electrical components inside the package are connected to stimulating leads by hermetic feedthroughs. However, where there is a need to couple an alternating electromagnetic field to an internal pickup coil, the metal becomes a hinderance. Transmission of power is substantially reduced by eddy currents generated in the metal due to the alternating electromagnetic field. To solve that problem, receiving coils are often placed outside the metal package, increasing the size of the implant.

It is known that glasses and ceramics are transparent to alternating electromagnetic fields and that receiving antennas can be placed inside a hermetic zone of a ceramic or glass package, creating an overall smaller implant device and reducing the possibility of antenna failure due to saline leakage. Glasses and ceramics are inert and highly insoluble, which are favorable characteristics for long term implant materials. Unfortunately, however, because glasses and ceramics are inelastic, they are subject to fracture not only from mechanical shock but also from differential thermal expansion if even a moderate temperature gradient exists thereacross. Therefore, welding is not a practical method of sealing glass or ceramic materials. Instead, virtually the entire package and its contents must be raised to the melting temperature of the glass or ceramic or metal braze used to effect a sealing of the glass or ceramic package. Such sealing methods are unsatisfactory. All known biocompatible glasses and ceramics are characterized by high sealing temperatures that will damage electronic components commonly included in electronic devices implanted in living bodies. Low melting temperature glasses all have the property of being corroded by body fluids. Further, metal or glass frits and solders useful in brazing glasses and ceramics and having melting temperatures below the thermal damage limits of implanted electronic components are either not biocompatible or corrode easily in body solutions. Therefore, packages composed entirely of ceramic and/or glass are not considered practical for such implant applications. Also, in prior ceramic and glass packages, the metal solder sealing the main body and cap portions of such packages has formed a closed loop very close to, coaxial with or in a plane parallel to the receiving coil comprising the antenna for the electronics housed in the implantable package. Thus configured, the closed metal loop of solder has acted as a shunt to the alternating electromagnetic fields impressed upon the package to transmit power and/or data to the implanted electronics. This has resulted in the generation of undesired heat within the package and the reduction of power transfer efficiency.

Therefore, there is a continuing need for a non-conducting hermetically-sealed package for electronic components which are damageable by high temperatures. The present invention satisfies that need.

SUMMARY OF INVENTION

The present invention comprises a package combination of one ceramic and two metal members hermetically sealed together where at least one metal member is characterized by a coefficient of linear thermal expansion substantially the same as the coefficient of linear thermal expansion for the ceramic and where the final package closure is effected by welding the two metal members together. Also, the junction between the ceramic and metal members of a first preferred package preferably comprises a bond of flat and smooth non-interlocking geometries. By such a design, forces resulting from unequal expansion or contraction of materials in or near the junction of the ceramic and metal members during temperature changes within and about the package are very inefficiently transferred to the ceramic member. This significantly reduces the risk of residual strain and ultimately of fractures in the ceramic.

Where the coefficients of linear thermal expansion of the ceramic and metal members are very close, the junction between the ceramic and metal members may be interlocking to effect a self-jigging of the members during assembly of a second preferred package of the present invention. In such a form of the package, temperature changes will produce corresponding changes in the geometries of the ceramic and metal members and undesired stresses on the junction will not occur.

More particularly, the first preferred package comprises a hollow flattened ceramic sleeve having a closed end and side wall portions and an open end for receiving electronic components of an implantable device which are adversely sensitive to high temperatures such as those components which receive and transmit electromagnetic energy from or to the outside of the package. Preferably, the coils comprising the antenna receiving and/or transmitting alternating magnetic fields are positioned within the ceramic sleeve remote from and in a plane transverse and preferably normal to a flat annular end face around the open end of the sleeve where a closed metal sealing band is located. In particular, the closed metal band has a flat annular edge hermetically sealed as by a biocompatible metallic braze or glass solder to the flat annular end face of the ceramic sleeve. Preferably, the band is formed of a metal having a coefficient of linear thermal expansion substantially the same as the ceramic material forming the sleeve. Thus configured, the closed metal loop formed by the metal band and/or metal solder does not act as a shunt to power and/or information conveying alternating electromagnetic fields impressed upon the package and antenna of the present invention.

Further, a header closes the package by means of an hermetic bond to the metal band and carries a plurality of electrical connectors for connecting electrical leads to the electronic components within the package. Preferably, the header comprises a metal sleeve circumscribing a ceramic header plate carrying the electrical connectors which are hermetically sealed in the header plate. The metal sleeve is bonded by high temperature welding, such as electron beam or laser welding, to the metal band after the electrical components are mounted in the ceramic sleeve and adequate heat sinking is applied to insure that there is no heat transfer to any heat-sensitive electronic components or ceramic package component during the hermetic sealing operation.

The present invention also comprises the method of assembly for the above-described package.

BRIEF DESCRIPTION OF DRAWINGS

FIG. 2 is a longitudinal sectional view of the package taken along the line 2—2 in FIG. 1.

FIG. 3 is a sectional top view of the package taken along the line 3—3 in FIG. 3.

FIG. 4 is an end view of the connector 21 shown in FIG. 1.

FIG. 6 is a longitudinal sectional view similar to FIG. 2 for a second preferred form of the package of the present invention.

FIG. 7 is a sectional top view similar to FIG. 3 of the package of FIG. 6.

FIG. 8 is an end view of a connector for the package shown in FIG. 7.

DETAILED DESCRIPTION OF INVENTION

Figure 1:
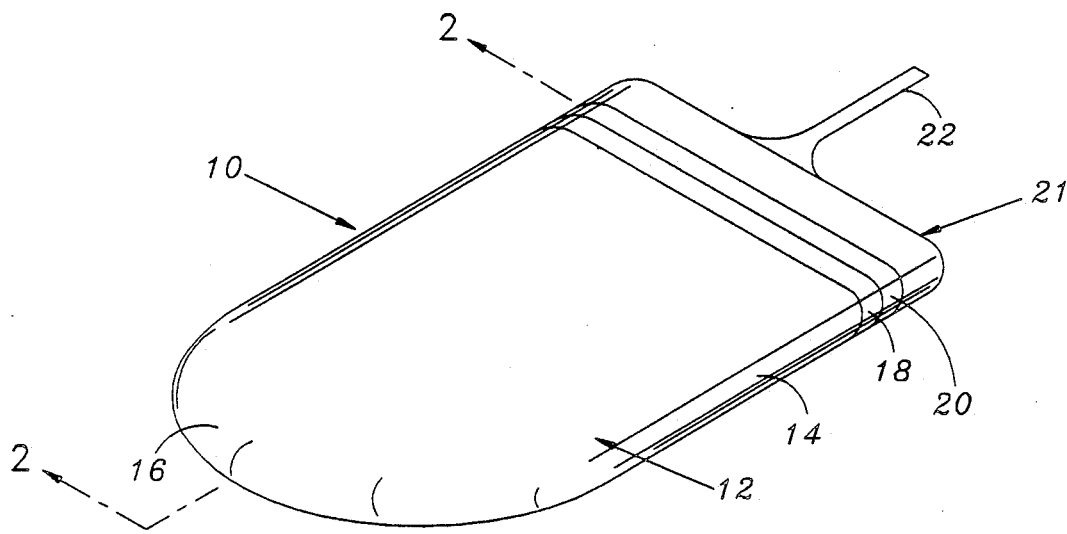
FIG. 1 is a perspective view of a first preferred form of the hermetically sealed combination ceramic and metal package of the present invention.

Generally speaking and as illustrated in FIG. 1, an implantable electronic device 10 comprises a hermetically sealed implantable package 12 including a flattened ceramic sleeve 14 having a closed end 16, a metal band 18 and a header 20 for closing the package and connecting via a cable connector 21 a plurality of electrical leads in a cable 22 to electronic components housed within the package.

More particularly, as shown in FIGS. 1 and 2, the sleeve 14 is formed of a ceramic material such as alumina or boron nitride (i.e. an inert ceramic) having a coefficient of expansion of about $7-8 \times 10^{-6}/^\circ$ C. The forward end of the sleeve is closed at 16 while a rear end of the sleeve is open at 24 and bounded or circumscribed by a flat annular end face 26 lying in a plane substantially normal to a longitudinal axis of the sleeve 14. The open end 24 of the sleeve is intended to receive electronic components of the implantable device 10, at least some of such components being subject to damage by high temperatures, e.g. above 150° C., and at least one of such components being an antenna 25 for receiving and/or transmitting electromagnetic energy (e.g., electrostatic and/or radio frequency). Preferably, the sleeve 10 forms a flat pocket-shaped structure with such electronic components housed adjacent the closed end 16 with the antenna 25 comprising transmitting and pick-up coils spaced from the open end 24 and coiling about an axis 38 transverse and preferably normal to the longitudinal axis of the sleeve 14. As will be described hereinafter, with such a spacing and geometric configuration for the antenna, the shunting effects of the band 18 and a metal solder upon the electromagnetic fields impressed on the package are minimized.

More particularly, the band 18 includes a flat annular edge 28 butting against and hermetically bonded t the end face 26 of the sleeve 14 and is formed of a metal having a coefficient of linear thermal expansion substantially the same as the ceramic material forming the sleeve 14. Preferably, the metal forming the band 18 is selected from the group consisting of niobium, molybdenum and tantalum having coefficients of linear thermal expansion between 6 and $8 \times 10^{-6}/^\circ$ C. Thus, the sleeve 14 and the band 18 will be subject to similar rates of linear expansion with temperature changes and forces tending to separate the sleeve and band at the junction therebetween will be minimal. Further, the bonding of the sleeve 14 and the band 18 preferably is by a butt brazing technique such as described hereinafter which eliminates the risk of cracking the ceramic sleeve at corner junctions between dissimilar geometries.

Generally speaking, the ceramic sleeve 14 may be formed to any desired shape and dimensions by processes well know to those skilled in the ceramic forming arts. Likewise, well known processes may be utilized to bond the band 1B to the end face 26 of the sleeve 14 utilizing biocompatible sealing materials. Preferably, however, such joining is accomplished by means of a butt braze using an alloy of about 71.5% titanium and 28.5% nickel by weight and the processing of the sleeve 14 and metal band 18 is according to the method illustrated in FIG. 5. As there depicted, to hermetically bond the band 18 to the end face 26 of the sleeve 10, the sleeve is first fired by placing the sleeve in an oven and slowly raising the temperature for example to about 1700° C. and holding the sleeve at that temperature for about 4 hours and then slowly cooling the sleeve to room temperature. Next, the annular end face 26 is ground smooth and flat as with a diamond grinder and any micro-cracks in the end face sealed by repeating the firing process described above. Following the cooling of the sleeve 14, the surface thereof may be cleaned, if necessary, by again placing the sleeve in the oven at about 1000° C. for several hours to remove any organic materials and contaminants from the surface thereof. Next, if the selected bonding material, such as the brazing alloy, is known not to adequately wet ceramic surfaces, it may be desired to metalize the end face 26 by coating it with a metal known to provide a good interface between the ceramic material comprising the sleeve 14 and the bonding material used to create the hermetic seal and bond between the end face 26 and the metal band 18. For example, if gold is used as the bonding material e.g a gold alloy foil, after masking all but the end face 26, niobium may be sputtered in a conventional manner onto the end face in a vacuum container.

Figure 5:
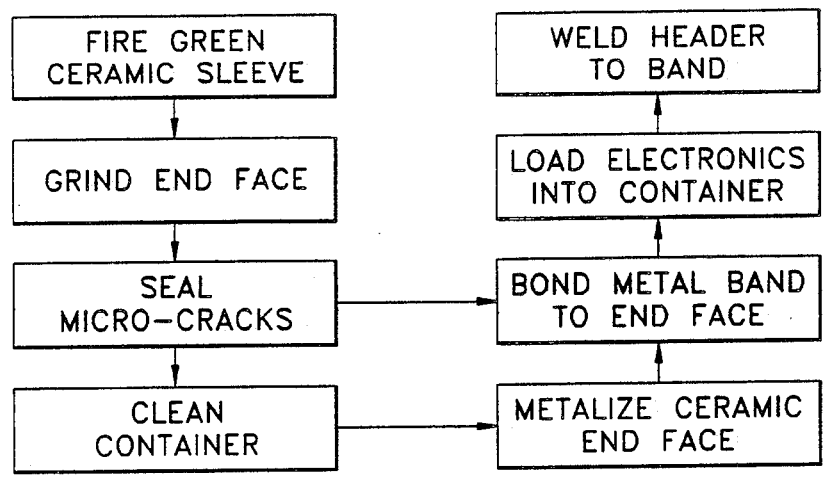
FIG. 5 is a flow diagram of a preferred form of the method of assembly of the package of FIG. 1.

After any micro-cracks have been sealed and any necessary cleaning and metalizing of the end face 26, the ceramic sleeve 14 and metal band 18 are placed in suitable fixtures with an annular foil of brazing alloy e.g. titanium and nickel, between the end face and the band. The combination is placed in a vacuum furnace, for example at about 15 microtorr, and the temperature of the furnace is slowly ramped to a temperature sufficient to melt the brazing alloy, e.g. about 1070° C. for gold. The combination is held at that temperature for about 2 minutes and then the temperature of the furnace is ramped down at about the same rate. This process creates a strong hermetic seal between the end face 26 and the metal band 18 which will withstand temperature changes during the balance of the assembly process as represented in FIG. 5 including the attachment of the header means 20 to the band 18. At this point it should be noted that the connection and sealing of the ceramic sleeve 14 and metal band 18 occurs at high temperatures, but out of the presence of electronic components which certainly would be damaged at such temperatures. Rather, as will be described, the electronic components are carried by a substrate connected to the header means 20 which is next connected to the band by a weld means which confines the high temperature to the immediate weld area.

More particularly, as represented most clearly in FIGS. 2 and 3, the header means 20 preferably closes and hermetically bonds to the metal band 18 and carries a plurality of electrical connectors 30 for connecting electrical leads to the electrical components housed within the sleeve. In addition, the header preferably supports a flat plate-like substrate 32 upon which the components are mounted. As shown, the substrate 32 extends through the open end 24 of the sleeve 14 into the interior thereof such that the substrate lies in a plane substantially parallel to the longitudinal axis of the sleeve. Thus positioned, the axis 33 of the coils comprising the antenna 25 is substantially normal to the plane of the substrate and hence the axis of the sleeve and substantially parallel to the end 26 of the sleeve.

To provide hermetic bonding to the band and electrical contact between the substrate and the outside of the package 12, the header means 20 preferably comprises a ceramic header plate 34 carrying the connectors 30 and an outer metal sleeve 36. The connectors are hermetically sealed to and extend through the header plate 34. This may be accomplished by a glass seal around the connectors within the plate by a co-firing of the metal pins comprising the connectors when the ceramic header is fired or by other means known to those skilled in the art. In the preferred design, the ceramic header plate is hermetically joined to the metal header sleeve by the same processes useful to join the ceramic sleeve and metal band as previously described.

The metal sleeve 36 is preferably formed of the same metal as the band 18 and includes an axially extending flange 38 at its innermost surface 40 facing the band. In fact, the inner surface of the band slightly overlies and engages the flange 38 to define an annular joint 42 between the band and the flange. Thus configured, upon the application of a narrowly confined high temperature weld, e.g. a laser or electron beam weld, at the outer annular surface of the band 18, that is at the end remote from the bond between the band 18 and the sleeve 14 and preferably over the annular joint 42, a hermetic seal and bond is formed between the band and the sleeve. Preferably, the welding of the sleeve to the band is accompanied by adequate heat sinking and by prudent application of heating energy to avoid overheating the package 12. For example, copper heat sink fixtures may be placed around the band and sleeve during the welding operation and the weld first may be at a first side wall of the band followed by a welding at an opposite side wall of the band, followed by a welding at a first top section of the band, followed by a welding at an opposite bottom section of the band and so on. This process minimizes the heating of the combination during the welding operation.

In addition to the axial flange 38 the sleeve 14 includes an annular radially inward directed flange 44 against which the header plate 34 bears during the bonding of the header plate to the sleeve. In this regard, such bonding is accomplished by the same process step as the bonding and sealing of the band 12 to the sleeve 14. That is, if necessary, a metal such as niobium is applied to the outer annular surface 46 of the header plate 34 as by sputtering in a vacuum container at about 15 microtorr. An annular foil of brazing alloy is placed between the outer annular surface 46 of the header plate and the inner surface 40 of the sleeve 36 and the combination placed in fixtures and secured in a vacuum furnace. The temperature of the furnace is then ramped up to the brazing temperature and then back to room temperature to create the bond and hermetic seal between the header plate and the sleeve.

As previously noted, and as most clearly depicted in FIGS. 2 and 3, when the package 10 is assembled as previously described, the electrical components, including the antenna 25, are spaced laterally from the end face 26 of the ceramic sleeve 14 and the resulting metal bond between the end face 26 and the annular end 28 of the metal band 18. Also, the axis 33 of the antenna 25 is preferably normal to the plane of the substrate 32. This means that the coils comprising the antenna lie in planes substantially parallel to the substrate and normal to the metal braze between the surfaces 26 and 28 defining a closed metal loop. Thus configured, and with the antenna 25 spaced from the metal braze, magnetic fields impressed upon the package 10 and received by the antenna 25 along directions parallel to the axis 33 are not shunted, or minimally so, by the closed loops defined by the metal braze and/or metal band 18. Thus, with the illustrated configuration of the package 10, undesired heat and loss of energy transfer efficiency are minimized.

As also illustrated in FIGS. 1 through 4, the electrical connection to the electronic components carried by the substrate 32 including the antenna 25 is via the electrical connectors 30 when coupled to the cable connector 21. The cable connector 21 shown in FIG. 4 comprises an elongated cup-shaped housing 48 carrying a socket structure 50 including a plurality of sockets 52 spaced to receive the connectors 30 extending from the package 12. When positioned over the end of the package 12, the connectors 30 extend into the sockets 52 and the connector 21 is secured to the package by suitable screw members passing through openings 54 in the connector 21 and into threaded holes 56 in the end face of the metal sleeve 36.

A similar cable connector, also bearing the numeral 21, is illustrated in FIG. 8 for use with a second form of the package 12 as illustrated in FIGS. 6 and 7. As there represented, the connector 21 includes an open, cup-shaped cover member 48 carrying a plurality of separate socket members 50, each having four sockets 52 for receiving groups of four connectors 30 extending from the header means 20 illustrated in FIGS. 6 and 7. But for the different header means 20, the package 12 illustrated in FIGS. 6 and 7 closely resembles and bears the same referenced numerals as the package 12 illustrated in FIGS. 1, 2 and 3.

In FIGS. 6 and 7, the header means 20 comprises a relatively thin metal plate 56 having it inner face recessed at an annular outer edge to define a step 58 for fitting into and forming an annular junction 42 similar to that illustrated in FIGS. 2 and 3. Thus positioned, the plate 58 closes the open end of the metal band 18 and may be secured thereto by the same welding process previously described to secure the sleeve 36 to the metal band 18.

As illustrated in FIGS. 6 and 7, the metal plate 56 carries four insulators 60 each supporting four conductors 30 for mating with corresponding sockets 52 carried by the sockets 50 in the cable connector 21. With the connector 21 placed over the open end of the package 12 illustrated in FIGS. 6 and 7, the conductors carried by the cable 22 are connected to the electronic components carried by the substrate 32 via the sockets 52 and connectors 30 in the same manner as for the package 12 illustrated and described with respect to FIGS. 1 through 4.

Figure 9:
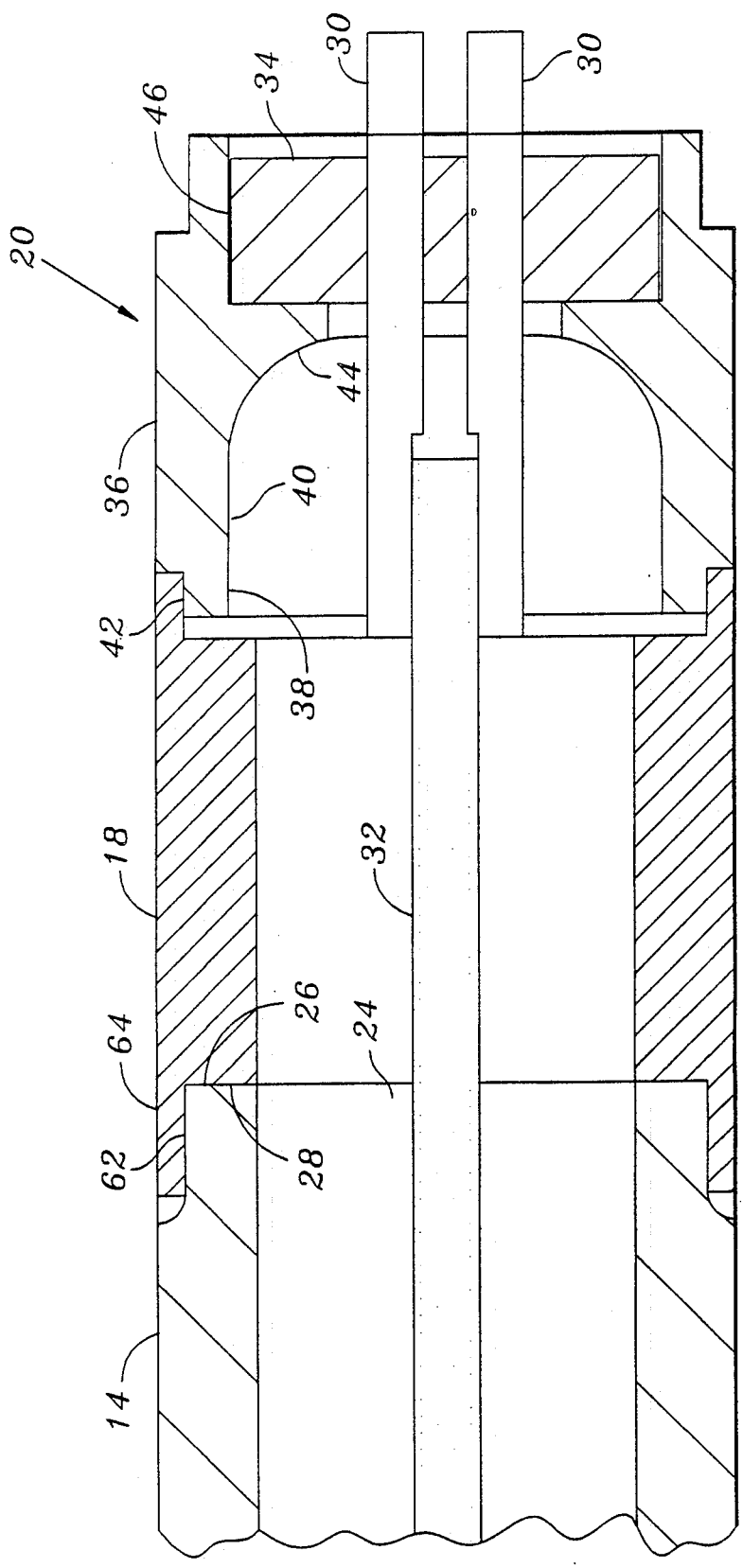
FIG. 9 is an enlarged fragmentary longitudinal sectional view of a self-jigging form of the package of the present invention including interlocking means between the junction of the metal and ceramic members of the package.

While it is preferred that the connection between the end face 26 of the ceramic sleeve 14 and the surface 28 of the metal band 18 be a butt connection, when the coefficients of linear expansion of the ceramic and metal materials comprising the sleeve and band are sufficiently similar, a step- or self-jigging configuration may be employed as illustrated most clearly in FIG. 9. As shown, the outer edge of the sleeve 14 may be relieved adjacent the end face 26 to form an annular step 62 for receiving an annular flange 64 extending from and common with the outer surface of the metal band 18. In such a configuration, the metal braze between the band 18 and ceramic sleeve 14 is located both between the end faces 26 and 28 and on the step 62. Of course, during the assembly of the metal band 18 to the ceramic sleeve 14, the annular step 62 cooperates with the annular flange 64 to guide and support a firm connection between the band and the sleeve. This is important in the rapid hand or mechanical assembly of the band to the sleeve.

While in the foregoing particular structures for hermetically sealed packages have been described in detail, it is to be appreciated that the present invention is not limited to the exact structure illustrated or the exact method of assembly described. Rather, the scope of the invention is to be limited only by the following claims.

We claim:

1. A hermetically sealed combination ceramic and metal package for electronic devices implantable in living bodies, comprising:
   a sleeve having a closed end and an open end for receiving electronic components of a device implantable in a living body, at least some of the components being adversely sensitive to high temperatures, the sleeve being formed of a ceramic material and the open end having a flat annular end face;
   a closed band having an annular edge butting against and hermetically bonded to the open-end face of the sleeve, the band being formed of a metal having a coefficient of linear thermal expansion substantially the same as that of the ceramic material forming the sleeve; and
   header means closing the package, hermetically bonded to the band and carrying a plurality of electrical connectors for connecting electrical leads to the electrical components within the sleeve.

2. The package of claim 1 wherein the annular end face of the sleeve and the annular edge of the band are flat to butt against each other.

3. The package of claim 1 wherein the annular end of the sleeve and the annular edge of the band are stepped to define a self-jigging junction between the sleeve and the band.

4. The package of claim 1 further including a cable connector releasably secured to the header means and comprising a plurality of sockets receiving the electrical connectors.

5. The package of claim 4 wherein the cable connector is secured by screws to the header means.

6. The package of claim 1 wherein the electrical connectors are hermetically sealed to the header means.

7. The package of claim 1 wherein the ceramic is an inert ceramic and the metal comprising the band is selected from the group consisting of niobium, molybdenum and tantalum.

8. The package of claim 1 wherein the annular end of the band is bonded by a metal or metal alloy braze to the annular end face of the sleeve.

9. The package of claim 1 wherein the header means carries a substrate supporting electronic components including an antenna within the sleeve remote from the open end.

10. The package of claim 9 wherein the antenna has an axis substantially parallel to the end face of the sleeve.

11. The package of claim 1 wherein the header means includes a ceramic header plate carrying the plurality of electrical connectors and enclosed within a metal sleeve hermetically bonded to the metal band.

12. The package of claim 11 wherein the metal sleeve carries an axially extending annular flange within and bonded to an annular surface of the metal band to create a hermetic seal therebetween.

13. The package of claim 12 wherein the metal sleeve carries a radially and inwardly extending annular flange and wherein the ceramic header plate bears against the radially extending flange with an annular outer edge of the header plate bonded to an inner annular surface of the metal sleeve.

14. The package of claim 13 wherein the outer edge of the ceramic header plate is bonded by a metal or metal alloy braze to the inner annular surface of the metal sleeve.

15. The package of claim 1 wherein the header means includes a metal header plate carrying the plurality of electrical connectors.

16. A method of assembly for a hermetically sealed combination ceramic and metal case for electronic devices implantable in living bodies, the method comprising the steps of:
bonding an annular face of a metal band to an end face of an open end of a ceramic sleeve having a closed end and the open end for receiving electronic components of an implantable electronic device, the band having a coefficient of linear thermal expansion substantially the same as that of the ceramic forming the sleeve;
loading electronic components carried by a header plate through the open end, the header plate closing the metal band and carrying a plurality of electrical connectors for connecting electrical leads to the electronic components housed within the sleeve; and
welding the header plate to the metal band to hermetically seal the open end of the ceramic sleeve.

17. The method of claim 16 further comprising the steps of:
firing the ceramic sleeve;
grinding the annular end face of the open end of the sleeve such that at least a portion of the end face is flat and smooth; and
sealing micro-cracks in the end face caused by the grinding thereof.

18. The method of claim 17 wherein firing the ceramic sleeve comprises slowly raising the temperature of the sleeve to and holding the temperature at about the sintering temperature for the ceramic and then slowly cooling the sleeve.

19. The method of claim 18 wherein the sealing of any micro-cracks in the end face comprises refiring the ceramic sleeve pursuant to claim 14.

20. The method of claim 17 further including the step of cleaning of the surface of the sleeve after sealing any micro-cracks by firing the sleeve at about 1000° C. to remove organic material and contaminates.

21. The method of claim 17 further including the step of coating of the end face of the sleeve after sealing any micro-cracks by masking all but the end face of the sleeve and sputter coating the end face with a metal or metal alloy braze under a vacuum.

22. The method of claim 17 wherein the bonding of the metal band to the ceramic sleeve comprises placing a metal or metal alloy foil between the end face of the sleeve and an annular end of the band, mounting the sleeve and band in fixtures with the end face butting against the annular end of the band and slowly heating the sleeve and band under a vacuum to the sintering temperature of the foil and then slowly lowering the temperature.

23. The method of claim 17 wherein, the welding of the header plate to the metal band comprises welding at an annular surface of the band around an annular axially extending surface o the header plate to create an internal hermetic seal between the band and plate.

24. The method of claim 23 wherein the welding is accomplished in a series of welding steps at spaced sections of the band accompanied by heat sinking.

* * * * *